(12) United States Patent
Marmaropoulos et al.

(10) Patent No.: US 7,210,939 B2
(45) Date of Patent: May 1, 2007

(54) CONDUCTIVE BUTTONHOLE INTERCONNECT

(75) Inventors: George Marmaropoulos, Yorktown Heights, NY (US); Giang Vu, Ossining, NY (US); Jack Kyriakos Mama, London (GB)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/568,437

(22) PCT Filed: May 13, 2004

(86) PCT No.: PCT/IB2004/001617

§ 371 (c)(1),
(2), (4) Date: Nov. 15, 2005

(87) PCT Pub. No.: WO2004/100691

PCT Pub. Date: Nov. 25, 2004

(65) Prior Publication Data

US 2006/0246744 A1 Nov. 2, 2006

Related U.S. Application Data

(60) Provisional application No. 60/471,702, filed on May 19, 2003.

(51) Int. Cl.
*H01R 33/00* (2006.01)

(52) U.S. Cl. .................. 439/37; 2/69; 2/905; 200/511

(58) Field of Classification Search ................ 439/37, 439/110; 219/211; 2/2.14, 902, 905, 906, 2/69; 126/204; 200/511
See application file for complete search history.

(56) References Cited

U.S. PATENT DOCUMENTS

| | | | | |
|---|---|---|---|---|
| 2,285,083 A | * | 6/1942 | Cover, Sr. ................. 455/90.3 |
| 2,287,915 A | * | 6/1942 | Taylor ........................ 219/211 |
| 2,458,119 A | * | 1/1949 | Van Daam .................. 219/211 |
| 4,539,700 A | | 9/1985 | Sato |
| 5,440,444 A | * | 8/1995 | Adams ........................ 361/220 |
| 5,613,756 A | * | 3/1997 | Allen .......................... 362/103 |
| 6,026,512 A | * | 2/2000 | Banks .............................. 2/69 |
| 6,642,467 B2 | * | 11/2003 | Farringdon ................. 200/511 |
| 6,925,654 B2 | * | 8/2005 | De Silva ........................ 2/108 |

FOREIGN PATENT DOCUMENTS

| | | |
|---|---|---|
| GB | 2364827 | 2/2002 |
| WO | WO199724042 | 7/1997 |

* cited by examiner

*Primary Examiner*—Michael C. Zarroli

(57) ABSTRACT

A wearable garment incorporates a manual interconnect device, so that a user wearing the garment can operate the interconnect device by coupling a connector, which is in turn coupled to a power source or external electronic device. Through a releasable locking action by the user, the connector is electrically coupled to the interconnect device, which is coupled to a fabric circuit integrated in the garment, such that operation of a locking action activates related ancillary equipment such as power supplies or electronic devices.

11 Claims, 3 Drawing Sheets

CONDUCTIVE BUTTONHOLE INTERCONNECT

CROSS REFERENCE TO RELATED APPLICATION

This application claims the benefit of U.S. provisional application Ser. No. 60/471,702 filed May 19, 2003, which is incorporated herein by reference.

This invention relates to an interconnect system intended to permit the connection of an electronic device or power source to a fabric electric circuit embedded in a garment. More specifically, the invention relates to an electrical interconnect system having an electrical interconnect device incorporated into the garment in a location or locations most conveniently accessible to the wearer.

Integrated electrical switches for use in clothing are typically sewn, glued, or otherwise mounted to clothing using standard "off the shelf" electric components, deemed well known in the art. However, to the best of the current inventors' knowledge, the prior art devices in wearable electronic applications do not address the problem of assuring simple and intuitive electrical connectors so as to be fashionable.

Therefore, the present invention relates to garment electrical connectors that can be realized in simple, intuitive, reliable, and inexpensive implementation. Moreover, the present invention facilitates manufacture of such connectors as close as possible to the manufacturing techniques used in the garment industry for widespread acceptance within the garment manufacturing industry.

The present invention discloses a wearable garment with an electrical interconnect system, which includes a buttonhole having at least one conductive outer edge mounted to the body of the garment and a connector detachably coupled to the conductive areas of the buttonhole for coupling an external electronic device or power source. The electrical interconnect system of this invention incorporates a buttonhole that can be easily manufactured with conventional buttonhole machines. The buttonhole is electrically coupled to a fabric circuit integrated in the garment material.

According to one aspect of the invention, a garment of desired form and function can be constructed in a conventional manner using readily available fabrics and materials, and the electrical interconnect system can be positioned advantageously within a buttonhole that permits easy activation manually by a person. Necessary connection cables or cords can extend from the interconnect system for connection to an electronic device embedded in the garment material or an external power source.

According to another aspect of the invention, a button having at least one conductive outer edge is attached to a first garment layer, which in turn is electrically coupled to a first fabric circuit integrated in the garment material. The button is releasably coupled to a button hole having at least one conductive outer edge attached to a second fabric circuit integrated in a second garment layer, such that the first and second fabric circuits of the respective layers can be electrically coupled together.

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

Figure 1:
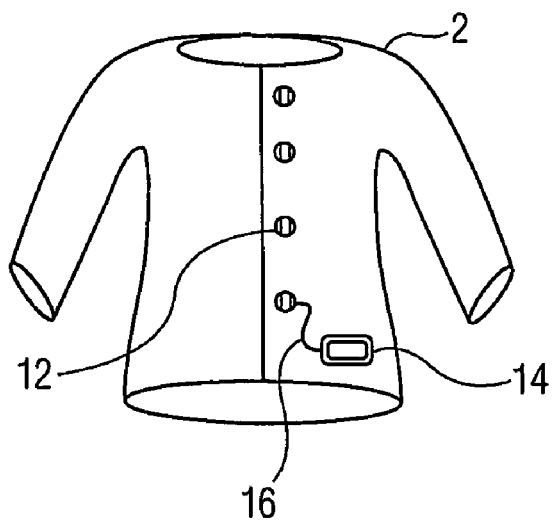
FIG. 1 illustrates an embodiment of an electrical interconnect system in accordance with this invention.

Referring now to FIG. 1 of the drawings, a wearable garment 2 in accordance with this invention includes an electrical interconnect device 12 and a connector 16. The connector 16 comprises a cable extending from the interconnect device 12, with the cable being coupled to a power source or other external electronic device 14. In the embodiment illustrated in FIG. 1, the wearable garment 2 has the form of a conventional sleeveless top shirt, although it will be understood readily that the shirt alternatively may be either long-sleeved, short-sleeved, vest, or jacket, for example. In addition, the materials of garment 2 may be either natural or synthetic, and the fabric created from such materials can be either woven or sheet-formed in any well-known manner.

Figure 2:
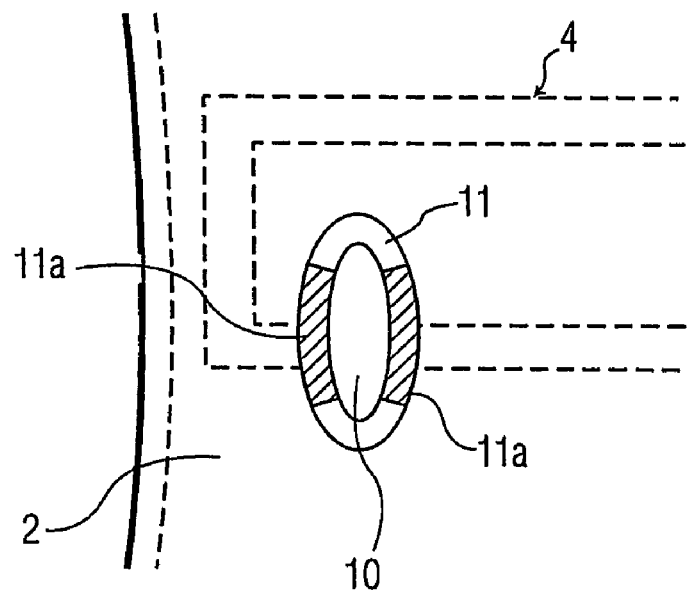
FIG. 2 illustrates the electrical interconnect system of FIG. 1 in accordance with a first embodiment of this invention.

Referring to FIG. 2, one side of the garment 2 is provided with the electrical interconnect system 12, which includes an opening 10 defined by an outer ring 11 having one or more conductive area (11a) at both ends thereof. The provision of the opening 10 to the fabric is well known to the skilled person, as are variations in such attachment detail. The outer ring 11 is electrically coupled to a conductive track of a fabric circuit 4, which may be provided in the form of loops to receive or otherwise engage equipment considered ancillary to the interconnect system 12, such as an external heart-monitoring device, external defibrillator, or other electronic devices. Alternatively, such ancillary equipment or other electronic devices may be integrated in the garment 2 and used in conjunction with the interconnect system 12 for transmitting the desired signals or power in any well-known manner.

Figure 3:
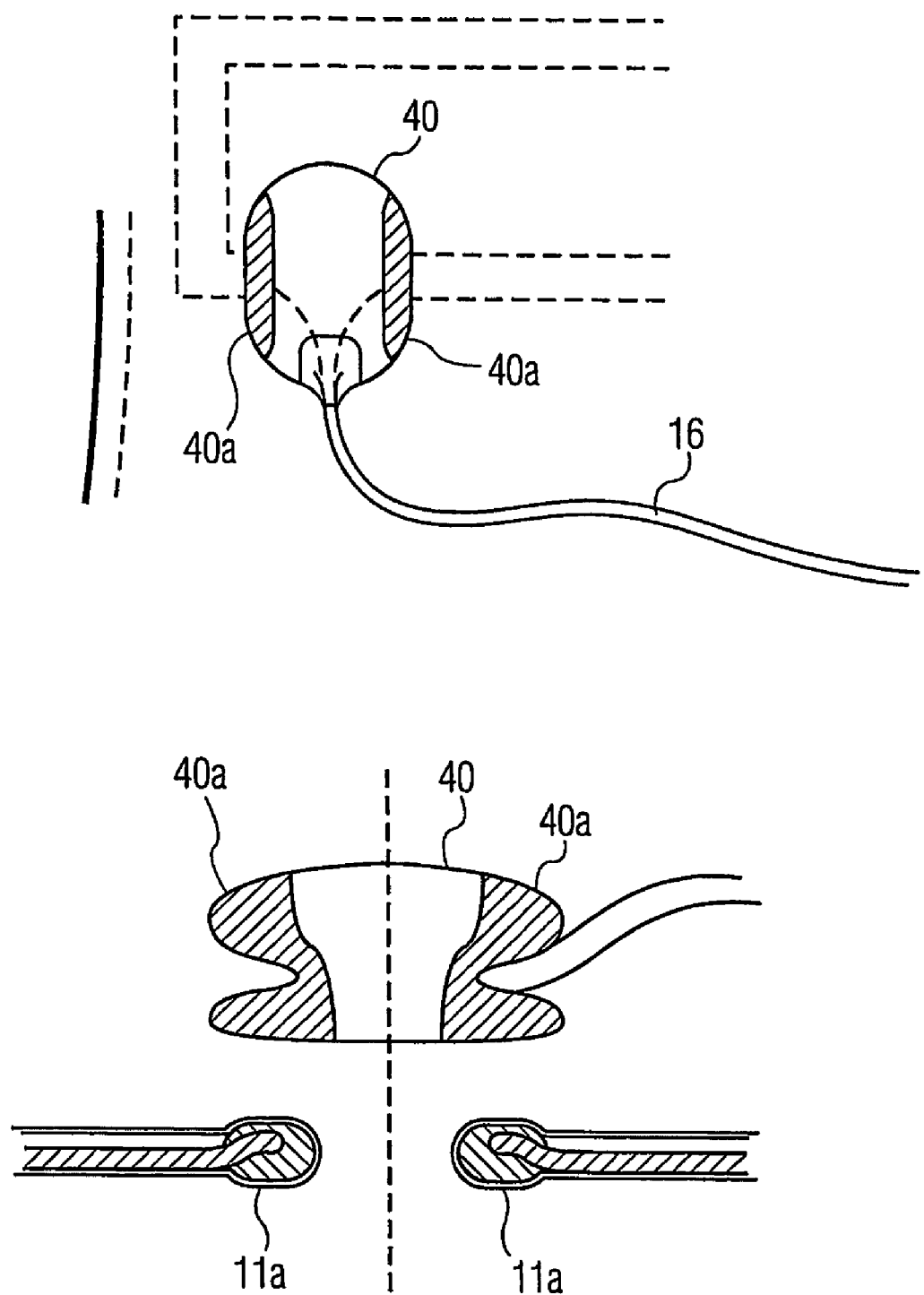
FIG. 3 is a detailed construction of the electrical interconnect system of FIG. 1 and a connector in accordance with the first embodiment of this invention.

Referring to FIG. 3, the connector 16 that allows the connection of a power supply or an external electronic device as described above comprises a button connector 40 having one or more conductive surfaces 40a that may be electrically coupled to the conductive areas (11a) of the outer ring 11 (See FIG. 2) for transmitting signals or power. As shown, the button connector 40 has a shape adapted to interconnect releasably the respective conductive areas physically and electrically with each other. Accordingly, a wearer can engage an ancillary device readily by merely mounting the button connector 40 with one hand to the proper opening 10 of the garment 2. It will be understood readily by those having skill in this art, that in this embodiment of the invention, any connecting cable 16 extending from the button connector 40 can be coupled without difficulty to an ancillary device such as a cell phone, radio, pager, GPS device, personal communication assistant, or other signal transmitter or duplex interactive system, carried anywhere on the person of the wearer of the band.

Figure 4:
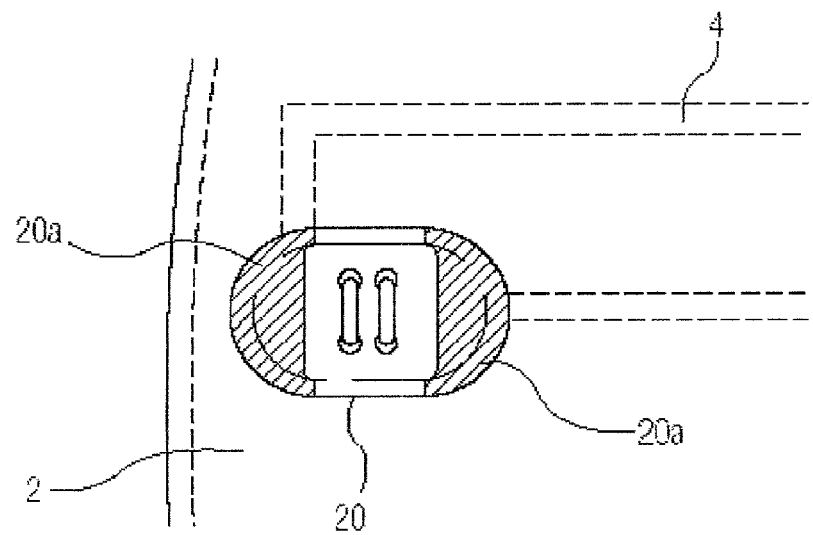
FIG. 4 illustrates the electrical interconnect system of FIG. 1 in accordance with a second embodiment of this invention.

FIG. 4 illustrates the electrical interconnect system 12 according to another embodiment of this invention. As shown, one side of the garment 2 is provided with a button component 20 having one or more conductive area 20a. The conductive area 20a of the button component 20 is electrically coupled to a conductive track of a fabric circuit 4. It is noted that the button component 20 in proper position on garment 2 formed by ordinary garment materials can be accomplished easily using well-known sewing and or other fabric-attachment techniques. The materials of such garment may be either natural or synthetic, and the fabric created from such materials may be either woven or sheet-formed in any well-known manner.

Figure 5:
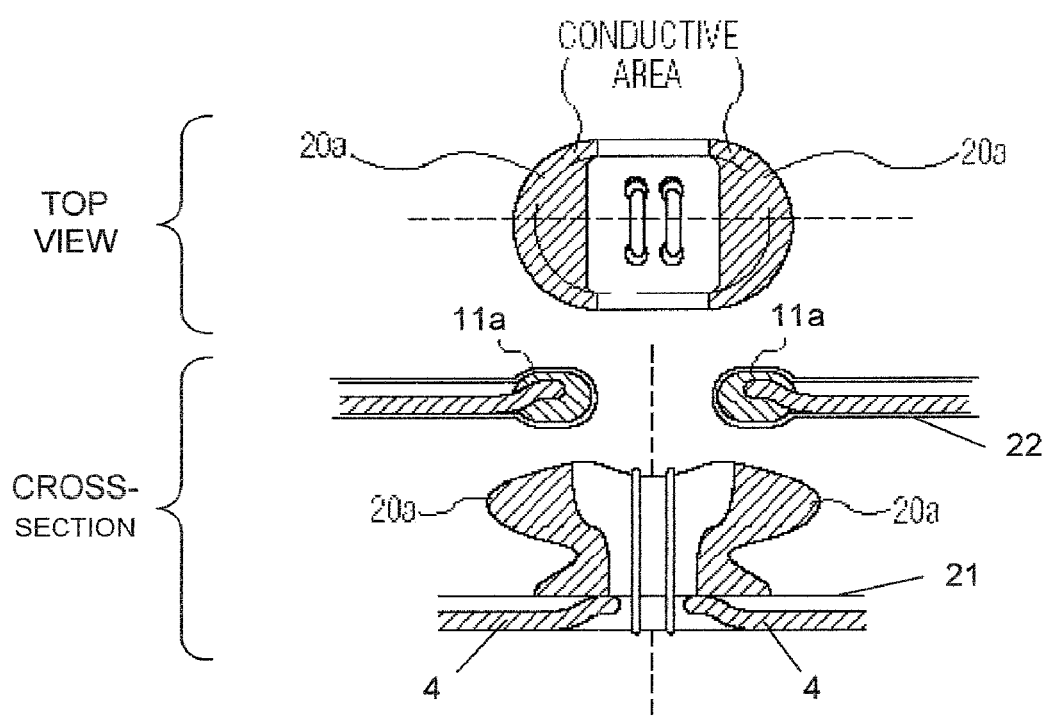
FIG. 5 is a detailed construction of the electrical interconnect system of FIG. 1 and a connector in accordance with the second embodiment of this invention.

Referring to FIG. 5, the button component 20 may be joined together with the outer ring 11 having conductive areas (11a) with a releasable locking action by the wearer. In this embodiment, a wearer can engage the interconnect system 12 readily by merely fastening the button connector 20 of a first layer 21 of the garment 2 to the outer ring 11 of a second layer 22 of the garment 2. The two layers joined together can be made to be water-resistant or waterproof in the area forming the interconnect system 12 to provide additional protection.

It should be noted that the conductive track of the fabric circuit 4 coupled to the button connector 20 may be provided in the form of loops to receive or otherwise engage equipment considered ancillary to the interconnect system 12, such as a heart-monitoring device, defibrillator, and other electronic devices that are integrated in the garment 2 and used in conjunction with the interconnect system 12 for transmitting the desired signals or power in any well-known manner.

While the preferred embodiments of the present invention have been illustrated and described, it will be understood by those skilled in the art that various changes and modifications can be made, and equivalents may be substituted for elements thereof without departing from the true scope of the present invention. For example, although an elliptical-shaped interconnect system is shown for illustrative purposes, it is to be understood that the present invention can support other shapes. Thus, the shape of an interconnect system in the drawings should not impose limitations on the scope of the invention. Therefore, it is intended that the present invention not be limited to the particular embodiment disclosed as the best mode contemplated for carrying out the present invention, but that the present invention include all embodiments falling within the scope of the appended claims.

What is claimed is:

1. An interconnect apparatus comprising:
   a wearable garment having a body structure;
   at least one interconnect element having a button hole opening defined by an outer ring, the outer ring having at least one electrically conductive contact portion wherein the interconnect element is coupled to a fabric circuit integrated in the garment via the at least one electrically conductive contact portion of the outer ring; and
   a button connector having at least one electrically conductive contact portion, the button connector having a shape adapted to be releasably coupled, physically and electrically, to respective at least one electrically conductive contact portion of the outer ring of the interconnect element.

2. The interconnect apparatus of claim 1, wherein the button connector has a cable extending therefrom.

3. The interconnect apparatus of claim 2, wherein the cable serves as a coupling to an electronic device.

4. The interconnect apparatus of claim 2, wherein the cable serves as a coupling to a power source.

5. The interconnect apparatus of claim 1, wherein the interconnect element is mounted on the outer surface of the garment for engaging and supporting units ancillary to transmitting electronic signals.

6. An interconnect apparatus comprising:
   a wearable garment having a body structure;
   at least one interconnect element having a button hole opening defined by an outer ring, the outer ring having at least one electrically conductive contact portion coupled to a first fabric circuit integrated in a first layer of the garment; and,
   a button connecting element having at least one electrically conductive contact portion coupled to a second fabric circuit integrated in a second layer of the garment,
   wherein interconnect element engages the button connecting element via a releasable locking action with button hole opening defined by outer ring so that the respective conductive contact portions come in contact electrically.

7. The interconnect apparatus of claim 6, wherein the first and second fabric circuits are coupled to a signaling device.

8. The interconnect apparatus of claim 6, wherein the first and second fabric circuits are coupled to electronic devices integrated in the body structure of the garment.

9. The interconnect apparatus of claim 6, wherein the button connecting element is a button having two separate electrically conductive portions, and wherein the outer ring has two separate electrically conductive contact portions, wherein a respective one of the electrically conductive portions of each of the button connecting element and the outer ring come in contact electrically in response to the interconnect element engaging the button connecting element via the releasable locking action.

10. A method for permitting a person to activate an electronic device conveniently, the method comprising the steps of:
    attaching at least one fabric circuit in a wearable garment;
    mounting an interconnect device having a button hole opening (10) defined by an outer ring, the outer ring having at least one conductive contact portion to the wearable garment;
    dressing the person in the wearable garment; and,
    selectively coupling a button connector having at least one conductive contact portion to the interconnect device via the at least one electrically conductive contact portion of the outer ring to serve as a coupling to an electronic device or a power source.

11. A method for permitting a person to activate an electronic device conveniently, the method comprising the steps of:
    attaching at least one fabric circuit in a first layer and a second layer of a wearable garment;
    mounting an interconnect device to the first layer of the wearable garment, the interconnect device having a button hole opening defined by an outer ring, the outer ring having at least one conductive contact portion electrically coupled to a conductive track of the first layer of the wearable garment;
    mounting a button connector to the second layer of the wearable garment, the button connector having at least one conductive contact portion electrically coupled to a conductive track of the second layer of the wearable garment;
    dressing the person in the wearable garment; and,
    enclosing the two layers of the wearable garment by engaging the button connector to the interconnect device via the at least one electrically conductive contact portion of the outer ring so that the respective conductive contact portions come in contact electrically.

* * * * *